(12) United States Patent
Li et al.

(10) Patent No.: US 12,312,287 B2
(45) Date of Patent: May 27, 2025

(54) METHOD AND DEVICE THEREOF FOR IMPROVING SELECTIVITY OF OXYGENATE CONVERSION TO LOW-CARBON OLEFIN

(71) Applicant: Luoyang Weida Petrochemical Engineering Co., LTD., Henan (CN)

(72) Inventors: Qunzhu Li, Henan (CN); Ruiyun Li, Henan (CN); Li Li, Henan (CN)

(73) Assignee: Luoyang Weida Petrochemical Engineering Co., LTD., Henan (CN)

( * ) Notice: Subject to any disclaimer, the term of this patent is extended or adjusted under 35 U.S.C. 154(b) by 407 days.

(21) Appl. No.: 17/775,519

(22) PCT Filed: Nov. 9, 2020

(86) PCT No.: PCT/CN2020/127548
§ 371 (c)(1),
(2) Date: May 9, 2022

(87) PCT Pub. No.: WO2021/089049
PCT Pub. Date: May 14, 2021

(65) Prior Publication Data
US 2022/0289643 A1    Sep. 15, 2022

(30) Foreign Application Priority Data
Nov. 9, 2019    (CN) .......................... 201911091130.X (51) Int. Cl.
*C07C 1/24*    (2006.01)
*B01J 8/18*    (2006.01)
(Continued)

(52) U.S. Cl.
CPC .............. *C07C 1/24* (2013.01); *B01J 8/1836* (2013.01); *B01J 8/24* (2013.01); *B01J 38/00* (2013.01); *C07C 2529/85* (2013.01)

(58) Field of Classification Search
CPC ......... C07C 1/24; C07C 2529/85; C07C 1/20; B01J 8/1836; B01J 8/24; B01J 38/00; B01J 8/26
(Continued)

(56) References Cited

U.S. PATENT DOCUMENTS 4,499,327 A    2/1985    Kaiser
6,166,282 A    12/2000   Miller
(Continued)

FOREIGN PATENT DOCUMENTS

CN    103804110 A    5/2014
CN    107428628 A    12/2017
(Continued)

OTHER PUBLICATIONS

International Search Report from International Patent Application No. PCT/CN2020/127548, mailed Jan. 6, 2021.

*Primary Examiner* — Prem C Singh
*Assistant Examiner* — Francis C Campanell
(74) *Attorney, Agent, or Firm* — Nitin Kaushik (57) ABSTRACT

Provided is a method for improving the selectivity of conversion of an oxygenate to low-carbon olefins. A regenerated catalyst from a regenerator enters a pre-hydrocarbon-pooling device where it comes into contact with an activation medium to undergo a pre-hydrocarbon-pooling reaction, forming "hydrocarbon pool" active species. The pre-hydrocarbon-pooled regenerated catalyst leaving the pre-hydrocarbon-pooling device enters a conversion reactor for recycling. By providing the pre-hydrocarbon-pooling device, and performing "pre-hydrocarbon-pooling" treatment on the regenerated catalyst, the regenerated catalyst is enabled to form "hydrocarbon pool" active species and carbon deposition before entering the conversion reactor. This improves the distribution of "hydrocarbon pool" active (Continued)

species and carbon deposition of the catalyst in the conversion reactor, thereby shortening or eliminating the "induction period" of the conversion reaction, and improving the catalytic activity and selectivity of the regenerated catalyst for a conversion of an oxygenate to low-carbon olefins.

20 Claims, 4 Drawing Sheets

(51) Int. Cl.
  *B01J 8/24* (2006.01)
  *B01J 38/00* (2006.01)
(58) Field of Classification Search
  USPC .......................................................... 585/639
  See application file for complete search history.

(56) References Cited

U.S. PATENT DOCUMENTS

| | | | |
|---|---|---|---|
| 2006/0025646 A1 | 2/2006 | Fung et al. | |
| 2018/0021769 A1* | 1/2018 | Li | B01J 8/20 |
| | | | 585/469 |

FOREIGN PATENT DOCUMENTS

| | | |
|---|---|---|
| CN | 111004077 A | 4/2020 |
| CN | 111018646 A | 4/2020 |
| CN | 111099945 A | 5/2020 |

* cited by examiner

METHOD AND DEVICE THEREOF FOR IMPROVING SELECTIVITY OF OXYGENATE CONVERSION TO LOW-CARBON OLEFIN

FIELD OF THE INVENTION

The present invention relates to a method and a device for improving the selectivity of conversion of an oxygenate to low-carbon olefins.

BACKGROUND OF THE INVENTION

Low-carbon olefins, defined herein as ethylene and propylene, are important basic organic chemical raw materials. With the sustained and rapid development of economy, the consumption of chemicals produced with ethylene and propylene as basic raw materials is increasing and the demand for these chemicals remains high. Ethylene and propylene are traditionally produced mainly from petroleum. However, due to the limited supply of petroleum resources and high prices thereof, the cost of producing ethylene and propylene from petroleum resources is constantly increasing. With the shortage of petroleum resources, it is of great significance to use non-petroleum raw materials to produce methanol, and then catalytically convert methanol to low-carbon olefins such as ethylene and propylene.

In recent years, people have begun to vigorously develop alternative energy conversion technologies, such as the oxygenates-to-olefins (OTO) process. Oxygenates include methanol, ethanol, dimethyl ether, methyl ethyl ether, etc. At present, there are many technologies that can be used to produce oxygenates, with raw materials including coal, natural gas, biomass, etc. For example, methanol can be obtained from coal or natural gas, and the process used has been very mature. Due to the wide range of sources of oxygenates, coupled with the cost effectiveness of using them in producing low-carbon olefins, more and more attention is being paid to the OTO process, especially the methanol-to-olefins (MTO) process.

Organic oxygenates, represented by methanol or dimethyl ether, are mainly produced from coal-based or natural gas-based synthesis gases. At present, processes for producing low-carbon olefins (mainly ethylene and propylene) with oxygenates (represented by methanol) as raw materials mainly include the MTO technology of U.S. UOP/Hyro company, the dimethyl ether/methanol-to-olefins (DMTO) technology of Dalian Institute of Chemical Physics, Chinese Academy of Sciences, and the methanol-to-propylene (MTP) technology of German Lurgi company.

The methanol-to-low-carbon-olefins process (referred to as MTO) is characterized by rapid reaction, strong heat release, low catalyst-to-methanol ratio, and reaction and regeneration in a continuous reaction-regeneration dense-phase fluidized bed reactor. High-temperature oil and gas rich in low-carbon olefins such as ethylene and propylene generated by the reaction need to be quenched and washed with water, and sent, after being removed of a catalyst entrained therein and being cooled, to a downstream olefin separation system for separation. Target products of the MTO process and unit are ethylene and propylene, and by-products thereof are ethane, propane, C5+ components, and fuel gases (dry gases), and the carbon-based yield of C4= is about 10%.

In recent years, MTO has become a hot spot and focus of research of industry insiders. Extensive research and exploration have been carried out in terms of processing flows, catalysts, process conditions, equipment structures, etc., with satisfactory results having been achieved, but there are few literature reports on how to improve the selectivity to low-carbon olefins.

As to the MTO technology, a certain amount of coke deposited on the SAPO-34 catalyst can greatly improve the yield of low-carbon olefins in reaction products (and the selectivity to low-carbon olefins is the highest when the coke deposited is in an optimal range). It is therefore necessary to properly control the amount of the coke deposited on the catalyst entering a conversion reactor, so as to achieve the purpose of improving the selectivity to low-carbon olefins. In addition, for a catalyst for which an optimal amount of coke deposited thereon exists, the more uniform the coke is distributed in a catalyst bed, the higher the selectivity to low-carbon olefins is in products. How to realize the control of uniform distribution of coke deposited on a catalyst in an MTO reactor (zone) is therefore one of the keys to the improvement of the selectivity to low-carbon olefins.

U.S. Pat. No. 4,499,327 discloses detailed studies on the use of a silicoaluminophosphate molecular sieve catalyst for the methanol to olefins process, and it points out that SAPO-34 is the first choice for catalysts for the MTO process. SAPO-34 catalyst has high selectivity to low-carbon olefins and a high activity, and can enable the reaction time for conversion of methanol to low-carbon olefins to be less than 10 seconds, even to time within a reaction time range required by a riser reaction.

U.S. Patent No. 20060025646 relates to a method for controlling the amount of coke deposited on a catalyst in a reaction zone of an MTO reactor, according to which a portion of the coked catalyst (namely the spent catalyst) is passed to a regeneration zone to burn off the coke to form a regenerated catalyst, and the other portion of the coked catalyst is mixed with the regenerated catalyst and then returned to the reaction zone for continued reaction. In this method, however, the coke-difference between the two catalysts entering the riser reactor is so huge that the distribution of coke on the catalyst in the reactor is very uneven. In a reactor, both a catalyst with much coke thereon and a catalyst with little coke thereon are unfavorable for the selectivity to low-carbon olefins, and may lead to decreased selectivity to low-carbon olefins and a decreased yield of target products (low-carbon olefins).

U.S. Pat. No. 6,166,282 discloses a method for converting methanol to low-carbon olefins, in which a fast-fluidized bed reactor is used. After completion of a reaction in a low-gas velocity dense-phase zone, a reaction gas, together with a catalyst entrained therein, rises to a fast separation zone where most of the entrained catalyst is initially isolated. Due to the rapid separation of the reaction product from the catalyst, occurrence of a secondary reaction is effectively prevented. Simulation calculations show that compared with a traditional bubbling fluidized bed reactor, the fast fluidized bed reactor has a greatly reduced inner diameter and a decreased required catalyst inventory. The carbon-based yield of low-carbon olefins according to this method is usually about 77%. The method also has the problem of low yield of low-carbon olefins.

The DMTO technology of Dalian Institute of Chemical Physics, Chinese Academy of Sciences employs a turbulent bed reactor which is operated at a relatively low gas velocity, usually 0.6-1.0 m/s. The carbon-based yield of low-carbon olefins according to this method is generally 78-80%.

In each of the above processes, the coke-difference between the regenerated catalyst entering the conversion reactor and the catalyst in the conversion reactor is very great (in a reactor, however, both a catalyst with much "carbon" thereon and a catalyst with little "carbon" thereon are unfavorable for the selectivity to low-carbon olefins). The above processes all have problems of poor selectivity to low-carbon olefins and low yield of low-carbon olefins.

Enormous research has shown that the MTO process follows the hydrocarbon pool mechanism, and active species in the hydrocarbon pool may be olefin species, aromatic species, or both of them play a role simultaneously. With an increase in the hydrocarbon pool active species in the molecular sieve, the shape-selective effect is enhanced; the activity of the reaction is significantly improved; and an autocatalytic property is exhibited. However, the catalytic hydrocarbon pool active species are not stable, and they may react further with olefins and the like to undergo condensed cyclization, leading to coking and deactivation of the catalyst.

In an existing regenerator, the coke-burning regeneration are usually carried out at a high temperature (550-800° C.). Research has shown that although the regenerated catalyst after the high-temperature regeneration still has "carbon", the "hydrocarbon pool" active species capable of catalyzing the conversion reaction of methanol to low-carbon olefins no longer exist after the high-temperature regeneration.

The induction period of catalyzing a conversion reaction of methanol lasts usually a few minutes, but the induction period of forming the "hydrocarbon pool" active species capable of the shape-selective catalyzing reaction of methanol to low-carbon olefins lasts tens of minutes or even hundreds of minutes. The later may be several dozens of times the former. As a result, catalyst beds in circulating fluidized bed reactors (zones) have the problem of uneven distribution of "hydrocarbon pool" active species.

However, conversion of methanol to hydrocarbons is a very complex reaction process, involving tens of thousands of reactions and intermediate products, and there may be hundreds of reaction paths. There are equilibrium reactions between olefin products, between aromatic hydrocarbon products, between olefins and aromatic hydrocarbons and other hydrocarbons, and conversion reactions between them are restricted by thermodynamic equilibrium as well as kinetics. Formation and types of "hydrocarbon pool" active species are therefore restricted by thermodynamic equilibrium and kinetics. The types and quantities (or contents) of "hydrocarbon pool" active species change, i.e., as long as reaction conditions change, the types and quantities of the "hydrocarbon pool" active species change. For example, "carbon" and "hydrocarbon pool" active species generated during a conversion reaction to $C_4^+$ (alkene) hydrocarbons at a high temperature (e.g., 530-600° C.) may not necessarily have the catalytic activity for a conversion reaction converting to low-carbon olefins under MTO reaction conditions (e.g., 470-480° C.). "Hydrocarbon pool" active species used for catalyzing a conversion reaction of methanol to hydrocarbons and "hydrocarbon pool" active species used for catalyzing a conversion reaction of methanol to low-carbon olefins are completely different or not exactly the same.

To sum up, "hydrocarbon pool" active species in industrially used circulating fluidized bed reactors are dynamically changeable (types and quantities thereof are changeable with the change of reaction conditions (mainly reaction temperatures)), and therefore catalyst beds have problems not only in the uneven distribution of carbon deposition, but also in the uneven distribution of "hydrocarbon pool" active species, which will inevitably affect catalytic activity and selectivity of conversion reactions of methanol to low-carbon olefins, which is actually the root reason for the low yield of low-carbon olefins in MTO units. For a long time, however, the foregoing problems have not caused people's attention, and so far have No any special research and reports.

Therefore, how to realize uniform distribution of "hydrocarbon pool" active species in MTO reactors (zones) (especially those "hydrocarbon pool" active species capable of improving the activity and selectivity of reactions of catalyzing oxygenates to low-carbon olefins under MTO conversion reaction conditions) is one of the keys to the improvement of the selectivity to low-carbon olefins.

In addition, there is a temperature difference of several hundred degrees (usually 150-300° C.) between the high-temperature regenerated catalyst directly entering the conversion reactor and the catalyst in the conversion reactor, which may cause local overheating of the catalyst bed (the high-temperature regenerated catalyst itself and its surroundings), leading to many secondary reactions, a large amount of coke-producing, and poor selectivity to low-carbon olefins in the conversion reaction process.

It is an objective of the present invention to perform, on the precondition of ensuring a good regeneration effect, "pre-hydrocarbon pooling" treatment on a regenerated catalyst by providing a pre-hydrocarbon pooling device (or a reaction zone), by means of which the sufficient time and space may be provided for a reaction of forming "hydrocarbon pool" active species capable of the shape-selective catalyzing of a conversion reaction of an oxygenate to low-carbon olefins. As such, the regenerated catalyst, before entering the conversion reactor, forms "hydrocarbon pool" active species capable of meeting requirements for conditions of the conversion reaction and having a good activity and good selectivity for catalyzing the reaction of preparing low-carbon olefins, so as to improve the activity and selectivity of the regenerated catalyst for use in the conversion reaction of the oxygenate to low-carbon olefins, and improve the distribution of "hydrocarbon pool" active species and coke-deposition of the catalyst in the conversion reactor. The present invention also uses a regenerated catalyst cooling technology to break thermal balance of the reaction-regeneration system. By providing a regenerated catalyst cooler, the temperature at which the regenerated catalyst enters the conversion reactor is reduced, which eliminates the problem of local overheating in the conversion reactor, optimizes temperature distribution in the conversion reactor, and further improves the yield of low-carbon olefins.

SUMMARY OF THE INVENTION

A technical problem to be solved by the present invention is to perform "pre-hydrocarbon pooling" treatment on a regenerated catalyst by providing a pre-hydrocarbon pooling device (or a reaction zone) to form "hydrocarbon pool" active species meeting requirements for conditions of a conversion reaction and having a good activity and good selectivity for use in the reaction of preparing low-carbon olefins, so as to improve the distribution of the "hydrocarbon pool" active species and coke-deposition of the catalyst in a conversion reactor, to thereby improve the activity and selectivity of the regenerated catalyst for the conversion reaction of an oxygenate to low-carbon olefins, and shorten or eliminate the "induction period" of the conversion reaction of the oxygenate to low-carbon olefins. Another technical problem to be solved is to reduce the temperature at which the regenerated catalyst enters the conversion reactor to eliminate local overheating in the conversion reactor and optimize temperature distribution in the conversion reactor (reaction zone), so as to further improve the activity and selectivity of the regenerated catalyst for the conversion of the oxygenate to low-carbon olefins (i.e. ethylene and propylene) to thereby further improve the yield of low-carbon olefins.

The present invention provides a method for improving the selectivity of conversion of an oxygenate to low-carbon olefins. A regenerated catalyst from a regenerator, after gas stripping, enters a pre-hydrocarbon pooling device, where the regenerated catalyst contacts with an activation medium to undergo reactions such as a pre-hydrocarbon pooling (or pre-activation) reaction to form "hydrocarbon pool" active species (and a certain amount of carbon deposition). The regenerated catalyst having undergone the pre-hydrocarbon pooling reaction leaving the pre-hydrocarbon pooling device (referred to as "pre-hydrocarbon pooled catalyst" or "pre-hydrocarbon pooled regenerated catalyst") enters a conversion reactor for recycling.

Main operating conditions of the pre-hydrocarbon pooling device (reactor) are as follows: a reaction temperature of 300-600° C. (preferably 360-560° C., more preferably 400-530° C.), and contact time of less than 300 minutes (preferably 0.001-200 minutes, more preferably 10-150 minutes).

The pre-hydrocarbon pooling device (reactor) includes a regenerated catalyst inlet (including a catalyst distributor), a regenerated catalyst outlet (for the pre-hydrocarbon pooled regenerated catalyst), an activation medium inlet (including a distributor), an activation medium outlet, or/and a fluidizing medium inlet (including a distributor).

The pre-hydrocarbon pooling device (reactor) adopts any one, two or more of various industrially used reactors, including fluidized bed reactors, moving beds, and fixed bed reactors, or a combination thereof. The fluidized bed reactors include bubbling bed reactors, turbulent bed reactors, fast bed reactors, riser reactors, etc. The riser reactors may be various industrially used equal-diameter or variable-diameter riser reactors. Preferably, the pre-hydrocarbon pooling device (reactor) adopts a low-velocity dense-phase fluidized bed having a superficial gas velocity (the ratio of the flow rate of the fluidizing medium to the cross-sectional area of the device) of less than 0.5 m/s (preferably 0.0001-0.3 m/s, more preferably 0.001-0.2 m/s).

The activation medium entering the pre-hydrocarbon pooling device may be any one, two or more of an oxygenate raw material, a reaction product, a hydrocarbon, and other oxygenates, or a mixture thereof.

The oxygenate raw material is any one, two or more of methanol, ethanol, dimethyl ether, and methyl ethyl ether, or a mixture thereof.

The reaction product may be a reaction gas that has not undergone a separation or has been removed of part or all entrained catalyst by a first-stage separator or multiple stages of separators (which may be cyclone separators, hydrocyclone separators, etc.), or a reaction gas that has undergone a heat-exchanging, quenching, or water washing, or a reaction gas from a downstream olefin product separation device (unit) pressurized by a reaction gas compressor, or a stripping gas (containing steam, reaction products, etc.) from a top of a sewage stripper, or any one, two or more of the foregoing, or a mixture thereof.

The hydrocarbon may be any one, two or more of products (including ethylene, propylene, ethane, propane, mixed C4, C5+ fractions, fuel gases, etc.) from the downstream olefin product separation device (unit), or a mixture thereof, or may be any one, two or more of various olefins, aromatic hydrocarbons, alkanes, or a mixture thereof.

The other oxygenates may be any one, two or more of any organic oxygenates (including various alcohols, ethers, esters, aldehydes, ketones, etc.), or a mixture thereof.

The catalyst may be any industrially used catalyst, including SAPO-34, ZSM-5 molecular sieve catalysts, and the like.

The pre-hydrocarbon pooling device may be provided outside or inside the conversion reactor, or may be in a one-piece structure with the conversion reactor, or may be connected to the conversion reactor through a conveying pipe. The specific structure, connection type, operating conditions, and control processes of the pre-hydrocarbon pooling device are very clear to those of ordinary skill in the art, and do not constitute limitations on any specific implementation of the inventive concept of the present invention.

In order to achieve a reaction temperature required for the pre-hydrocarbon pooling reaction, a regenerated catalyst cooler may be provided before the regenerated catalyst enters the pre-hydrocarbon pooling device to cool the regenerated catalyst to 200-630° C. (preferably 300-600° C., more preferably 360-600° C.).

Further, in order to realize optimal control of the reaction temperature of the pre-hydrocarbon pooling reaction or/and the reaction temperature of the downstream oxygenate conversion reactor, the regenerated catalyst cooler may be provided upstream of a regenerated catalyst stripper to strengthen mixing of the regenerated catalyst to eliminate a radial temperature difference caused by non-uniform heat-transferring and non-uniform flow, to thereby ensure a temperature balance in the regenerated catalyst, so as to meet requirements for temperature control of the pre-hydrocarbon pooling reaction and of the downstream conversion reaction and improve the accuracy and flexibility of the temperature control. In the case that the regenerated catalyst cooler is provided downstream of the regenerated catalyst stripper, a catalyst mixing buffer space has to be provided downstream of the regenerated catalyst cooler to eliminate a radial temperature difference caused by non-uniform heat-transferring and non-uniform flow to thereby realize a temperature balance in the regenerated catalyst.

The regenerated catalyst stripper or/and the regenerated catalyst mixing buffer space each adopt a low-velocity dense-phase fluidized bed having a superficial gas velocity (the ratio of the flow rate of the fluidizing medium to the cross-sectional area of the empty column of the device) of less than 0.5 m/s (preferably 0.0001-0.3 m/s, more preferably 0.001-0.2 m/s). A stripping medium or a fluidizing medium for the regenerated catalyst stripper or the catalyst mixing buffer space may be steam or other fluids, or a mixture thereof (preferably steam).

Specific structures, connection types, operation and control processes of the foregoing are very clear to those of ordinary skill in the art and do not constitute limitations on any specific implementation of the inventive concept of the present invention.

The reaction temperature of the pre-hydrocarbon pooling reaction or/and the reaction temperature of the conversion reactor are mainly controlled by adjusting a circulating amount of the regenerated catalyst (i.e., adjusting a control element such as a slide valve of the cold regenerated catalyst conveying pipe), or/and by adjusting a temperature of the cold regenerated catalyst, and/or by adjusting a heat extraction load of the heat extractor of the pre-hydrocarbon pooling reactor, to thereby maintain the temperatures at an optimum value, thereby optimizing the temperature distribution of the conversion reactor, further improving the selectivity of the conversion reaction, and improving the yield of target products such as low-carbon olefins. The temperature of the cold regenerated catalyst is controlled by adjusting a flow rate of the fluidizing medium entering the regenerated catalyst cooler and/or a flow rate of the cold catalyst returned to the regenerator and/or other parameters.

In order to better control the reaction temperature of the pre-hydrocarbon pooling reactor, the pre-hydrocarbon pooling reactor may also be provided with an internal heat extractor or an external heat extractor at an interior thereof or an exterior thereof to maintain the thermal balance of the pre-hydrocarbon pooling reaction system. The reaction temperature of the pre-hydrocarbon pooling reactor is controlled mainly by adjusting an amount of the regenerated catalyst returned to the pre-hydrocarbon pooling reactor, or/and a flow rate of a heat extracting medium, or/and a flow rate of the fluidizing medium, or/and other parameters.

The fluidizing medium may be air, steam, or other fluids, or a mixture thereof, and the heat-extracting medium may be water, steam, air, or other fluids, or a mixture thereof.

Of course, there may be many other control devices and control methods, which do not constitute limitations on any specific implementation of the inventive concept of the present invention.

Catalyst coolers are mature industrially used devices. The method and the device of the present invention may adopt various industrially used (including fluidized catalytic cracking units, MTO units, etc.) structural forms (such as up-flow, down-flow, etc.). Catalyst conveying pipes may adopt various specific connection structures (such as internal circulation pipes, Y-shaped, U-shaped external conveying (circulation) pipes, etc.), with or without degassing (balance) pipes. The selection and control of specific structures, connection types, operating parameters (such as superficial linear velocity) of the foregoing are very clear to those of ordinary skilled in the art and do not constitute limitations on any specific implementation of the inventive concept of the present invention.

The conversion reactor may be any one, two or more of various industrially used reactors, including fluidized bed reactors, moving bed reactors, and fixed bed reactors, or a combination thereof. The conversion reactor may be any one, two, or more of various industrially used (including fluid catalytic cracking units, MTO units, etc.) fluidized bed (including bubbling bed, turbulent bed, fast bed, etc.) reactors or riser reactors, or a combination thereof. The riser reactors may be various industrially used equal-diameter or variable-diameter riser reactors.

Fluidized bed (including riser) reaction-regeneration units are mature industrial processes, and various reactors, regenerators, internal or external catalyst coolers (referred to also as heat extractors, including up-flow, down-flow, back-mixed external heat extractors, etc.), steam (gas) strippers, catalyst distributors, steam (gas) gas distributors, and the like used by them can all be used in the present invention. Specific structures, combination types, operations, and control processes of the foregoing, as well as the selection and use of operating conditions (such as feed temperatures, reaction temperatures, reaction pressures, contact time, catalyst-methanol ratios (or catalyst-oil ratios, i.e., the ratio of the catalyst to the raw material, superficial linear velocity, etc.) and catalysts are very clear to those of ordinary skill in the art, and do not constitute limitations on any particular implementation of the inventive concept of the present invention.

In the use of the method and the device of the present invention, the conversion reaction conditions are conventional conditions, and the separation of the reaction products and the regeneration of the catalyst are all carried out according to conventional methods. The spent catalyst is regenerated in the regenerator by coke-burning under conventional regeneration conditions. The regeneration temperature is usually controlled at 550-800° C. (preferably 600-730° C., more preferably 650-710° C.). The conversion reaction temperature is usually 400-560° C. (preferably 420-520° C., more preferably 450-500° C.).

The method and the device of the present invention may adopt various industrially used (including fluid catalytic cracking units, MTO units, etc.) reaction-regeneration modes. Specific structures, combination types, operation, and control processes of the foregoing are very clear to those of ordinary skill in the art, and do not constitute limitations on any specific implementation of the inventive concept of the present invention.

Compared with the existing technologies, the present invention has the following advantages.

1. The method for improving the selectivity of conversion of an oxygenate to low-carbon olefins according to the present invention, by providing the pre-hydrocarbon pooling device, perform "pre-hydrocarbon pooling" treatment on the regenerated catalyst, so that the regenerated catalyst forms "hydrocarbon pool" active species and carbon deposition before entering the conversion reactor, by way of which the distribution of "hydrocarbon pool" active species and coke-deposition of the catalyst in the conversion reactor can be improved, and the "induction period" of the conversion reaction can thus be shortened or eliminated, and the catalytic activity and selectivity of the regenerated catalyst for the conversion reaction of the oxygenate to low-carbon olefins can be improved.

2. The use of the regenerated catalyst cooling technology breaks the thermal balance of the reaction-regeneration system, reduces the temperature of the regenerated catalyst entering the conversion reactor, and eliminates local overheating in the conversion reactor caused by the high temperature of the regenerated catalyst, making the temperature distribution of the bed in the conversion reactor more uniform. This enormously facilitates ideal reactions such as the conversion of the oxygenate to low-carbon olefins, and inhibits non-ideal reactions such as thermal polymerization of low-carbon olefins, thereby improving the selectivity of the reaction, further improving the yield of low-carbon olefins, and reducing the coking rate of the catalyst (i.e., the coke-difference between the regenerated catalyst and the spent catalyst).

3. The use of low-temperature regenerated catalyst circulation reduces hydrothermal deactivation of the regenerated catalyst during conveying (before being conveyed to the conversion reactor), improves the activity of the regenerated catalyst, and reduces consumption of the catalyst.

4. A catalyst mixing buffer space may be provided to strengthen the mixing of the catalyst to realize a balanced, uniform, and stable temperature of the regenerated catalyst, thereby improving the accuracy and flexibility of the temperature control of the pre-hydrocarbon pooling reaction and the downstream conversion reaction.

Meanwhile, this also effectively improves the density and buffering capacity of the regenerated catalyst, and improves the driving force of the regenerated catalyst circulation system, thereby enhancing the controllability, reliability, stability and flexibility of the operation, and realizing optimal control of the temperature of the conversion reaction and optimal control of the depth of the reaction.

5. The adjustment of operating conditions such as the reaction temperature of the conversion of the oxygenate to olefins and the circulation amount of the catalyst is relatively independent and more flexible. Flexible adjustment can therefore be made based on market conditions to achieve different product distributions.

6. The low-temperature regenerated catalyst may be used as a cold shock agent and directly enter a rapid separation device (including an inlet or an outlet) to achieve rapid termination of the conversion reaction. This can suppress non-ideal reactions such as thermal polymerization of low-carbon olefins, thus further improving the yield of low-carbon olefins and reducing the coking rate of the catalyst (i.e., the coke-difference between the regenerated catalyst and the spent catalyst). This, at the same time, can also realize pre-hydrocarbon pooling reaction of the reaction gas on the regenerated catalyst, to form hydrocarbon pool active species and carbon deposition, thereby shortening or eliminating the "induction period" of the reaction, improving the activity and selectivity of regenerated catalyst (used for the reaction of preparing low-carbon carbon olefins), and further improving the yield of low-carbon olefins.

BRIEF DESCRIPTION OF THE DRAWINGS

The present invention will be described in detail below with reference to the accompanying drawings. The accompanying drawings are drawn to illustrate the present invention and do not constitute limitations on any specific implementation of the inventive concept of the present invention.

DETAILED DESCRIPTION OF THE EMBODIMENTS

Figure 1:
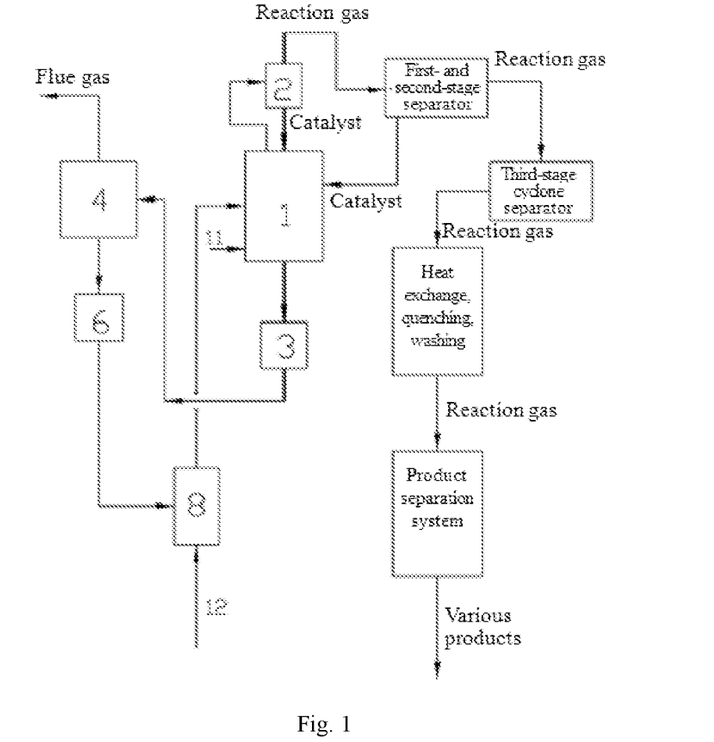
FIGS. 1 to 4 are typical schematic diagrams of methods and devices for improving the selectivity of conversion of an oxygenate to low-carbon olefins according to the present invention.

FIG. 1 is a schematic block and flow diagram of a method and a device for improving the selectivity of conversion of an oxygenate to low-carbon olefins according to the present invention (a pre-hydrocarbon pooling device is separately provided outside a conversion reactor).

As shown in FIG. 1, the method and the device for improving the selectivity of conversion of an oxygenate to low-carbon olefins according to the present invention include a (conversion) reactor 1, a rapid separation device 2, a spent catalyst stripper 3, a regenerator 4, a regenerated catalyst stripper 6, and a pre-hydrocarbon pooling device 8.

An oxygenate raw material 11 after preheating enters the (conversion) reactor 1 to come into contact with a catalyst to undergo a conversion reaction of an oxygenate to olefins. A reaction product and part of deactivated catalyst entrained therein go upward to the gas-solid rapid separation device 2 for a quick separation of the catalyst from the reaction product, then sequentially enter a first-stage separator and a second-stage separator (such as cyclone separators, etc.) for removal of the catalyst, and then a third-stage cyclone separator for further removal of traces of fine powder of the catalyst. The reaction gas, after sequentially going through a heat exchange, cooling, and water washing, enters a downstream product separation system for further separation, so as to obtain desired target products (such as ethylene, propylene, etc.) and by-products (ethane, propane, mixed C4, C5+ fractions, and fuel gases).

Main operating conditions of the conversion reactor 1 are as follows: a reaction temperature of 400-560° C. (preferably 420-520° C., more preferably 450-500° C.), a reaction pressure of 0.11-0.4 MPa, a weight ratio of the (circulated) regenerated catalyst to the raw material (namely catalyst-to-alcohol ratio) of 0.1-0.5 (preferably 0.12-0.3, more preferably 0.15-0.25).

The part of deactivated catalyst separated by the rapid separation device 2 and the first-stage and second-stage separators is returned to the conversion reactor 1. A spent catalyst from a reaction zone 22 of the conversion reactor 1, after being stripped by the spent catalyst stripper 3, enters the regenerator 4 for regeneration by coke-burning, so that the catalyst in the conversion reactor 1 can have an activity meeting requirements of the reaction.

The regeneration temperature is usually controlled at 550-800° C. (preferably 600-730° C., more preferably 650-710° C.).

A regenerated catalyst from the regenerator 4 passes through the regenerated catalyst stripper 6, and then enters the pre-hydrocarbon pooling device 8 where the regenerated catalyst contacts with an activation medium 12 to undergo chemical reactions such as pre-hydrocarbon pooling to form "hydrocarbon pool" active species and a certain amount of carbon deposition, so as to shorten or eliminate an "induction period" of the conversion reaction of the oxygenate to low-carbon olefins. The "pre-hydrocarbon pooled" regenerated catalyst leaving the pre-hydrocarbon pooling device 8 enters the conversion reactor 1 for recycling.

Main operating conditions of the pre-hydrocarbon pooling device (reactor) are as follows: a reaction temperature of 300-600° C. (preferably 360-560° C., more preferably 400-530° C.), and contact time of less than 300 minutes (preferably 0.001-200 minutes, more preferably 10-150 minutes).

In order to better control the reaction temperature of the pre-hydrocarbon pooling device 8, the pre-hydrocarbon pooling device 8 may be provided at an interior or/and an exterior thereof with an internal heat extractor or/and an external heat extractor (not shown in the figure) to maintain the thermal balance of the pre-hydrocarbon pooling reaction system. The reaction temperature of the pre-hydrocarbon pooling device 8 is mainly controlled by adjusting an amount of the regenerated catalyst returned to the pre-hydrocarbon pooling device, or/and a flow rate of a heat extracting medium, or/and a flow rate of a fluidizing medium, or/and other parameters.

Figure 2:
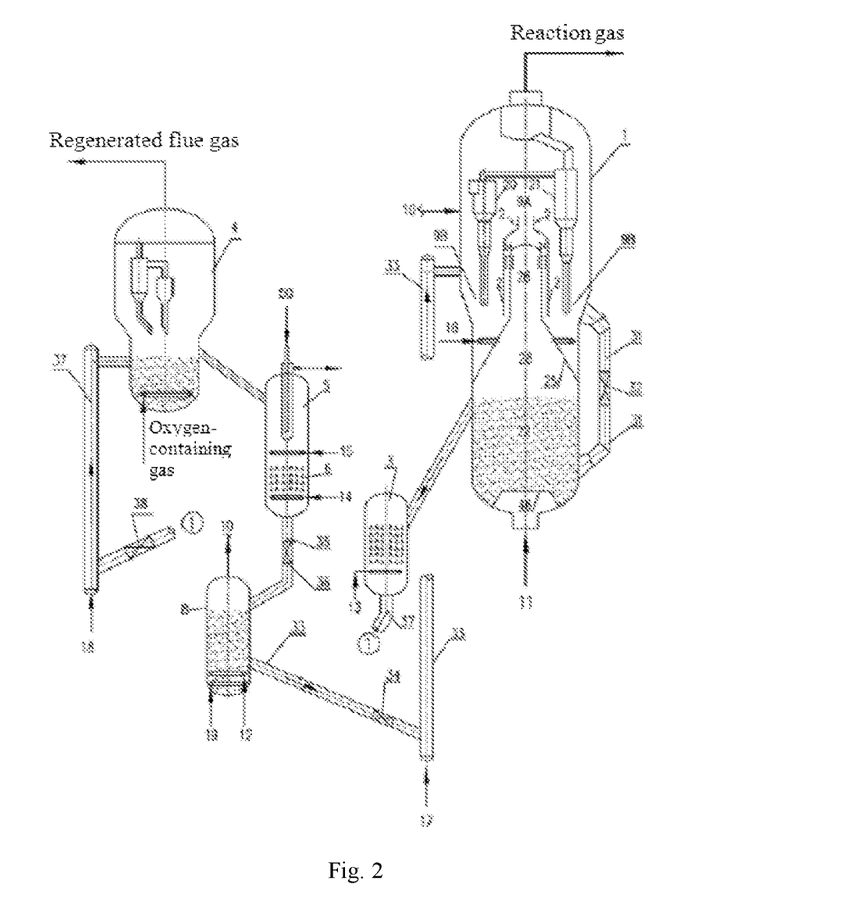

FIG. 2 is a schematic diagram of a process flow of a method and a device for improving the selectivity of conversion of an oxygenate to low-carbon olefins according to the present invention.

As shown in FIG. 1, the method and device for improving the selectivity of conversion of an oxygenate to low-carbon olefins according to the present invention include a conversion reactor 1, a rapid separation device 2 (including a hydrocyclone distributor 24), a spent catalyst stripper 3, a regenerator 4, a regenerated catalyst cooler 5, a regenerated catalyst stripper 6, and a pre-hydrocarbon pooling device 8.

A partition 25 is provided to separate a reaction zone 22 from a settling zone 9 (including a dilute phase zone 9A and a dense phase zone 9B). A reaction gas product produced in a reaction in the low-gas velocity reaction zone 22 and a catalyst entrained therein enter a reduced-diameter conveying pipe 26, rise, pass through the hydrocyclone distributor 24, and then tangentially enter the rapid separation device 2, for separation of most of the part of the deactivated catalyst entrained. The entrained catalyst separated by the rapid separation device 2 and first-stage and second-stage cyclone separators 20 and 21 enters the dense phase zone 9B of the settling zone 9.

An oxygenate raw material 11 after preheating enters the reaction zone 22 of the (conversion) reactor 1 through a distributor 46 to come into contact with a catalyst to undergo a conversion reaction of an oxygenate to olefins. A reaction product and a catalyst entrained therein go upward to the gas-solid rapid separation device 2 in the conversion reactor 1 for a quick separation of the catalyst from the reaction product, then sequentially enter the first-stage and second-stage cyclone separators 20 and 21 for removal of the spent catalyst, and then a third-stage cyclone separator for further removal of traces of fine powder of the catalyst. The reaction gas, after sequentially going through a heat exchange, cooling, and water washing, enters a downstream product separation system for further separation, so as to obtain desired target products (such as ethylene, propylene, etc.) and by-products (ethane, propane, mixed C4, C5+ fractions, and fuel gases).

Main operating conditions of the conversion reactor 1 are as follows: a superficial linear velocity of less than 1.2 m/s (preferably 0.5-1.0 m/s) in the reaction zone 22 of the conversion reactor 1, a reaction temperature of 400-560° C. (preferably 420-520° C., more preferably, 450-500° C.), a reaction pressure of 0.11-0.4 MPa, and a weight ratio of the (circulated) regenerated catalyst to the raw material (namely catalyst-to-alcohol ratio) of 0.1-0.5 (preferably 0.12-0.3, more preferably 0.15-0.25).

In order to effectively control the temperature of the conversion reaction, an internal heat extractor or/and an external heat extractor (not shown in the figure) is provided to remove excess heat produced during the conversion reaction.

The spent catalyst from the reaction zone 22 of the conversion reactor 1, after being stripped by the spent catalyst stripper 3, passes through a conveying pipe 37 (including a control valve 38 and a catalyst distributor (not shown in the figure)), and then enters the regenerator 4 for regeneration by coke-burning, so that the catalyst in the reaction zone 22 of the conversion reactor 1 can have an activity meeting requirements of the reaction The regeneration temperature is controlled at 600-730° C. (preferably 650-710° C.).

The regenerated catalyst from the regenerator 4 enters the regenerated catalyst cooler 5 for cooling to 200-630° C. (preferably 300-550° C., more preferably 360-500° C., most preferably 420-480° C.), passes through the regenerated catalyst stripper 6 (so that the temperature of the regenerated catalyst is balanced before entering the pre-hydrocarbon pooling device 8), and then enters the pre-hydrocarbon pooling device 8 through a regenerated catalyst conveying pipe 35 (including a control valve 36 and a catalyst distributor (not shown in the figure)). In the pre-hydrocarbon pooling device 8, the regenerated catalyst contacts with an activation medium 12 to undergo chemical reactions such as pre-hydrocarbon pooling to form "hydrocarbon pool" active species and a certain amount of carbon deposition, so as to shorten or eliminate an "induction period" of the reaction. The activation medium 12 passes through the regenerated catalyst bed from bottom to top, and the reaction gas after the pre-hydrocarbon pooling enters the dilute phase zone 9A at an upper portion of the settling zone 9 through a pipe 10.

Main operating conditions of the pre-hydrocarbon pooling device (reactor) are as follows: a reaction temperature of 300-600° C. (preferably 360-560° C., more preferably 400-530° C.), contact time of less than 300 minutes (preferably 0.001-200 minutes, more preferably 10-150 minutes).

The pre-hydrocarbon pooling device (reactor) preferably adopts a low-velocity dense-phase fluidized bed having a superficial gas velocity of less than 0.5 m/s (preferably 0.0001-0.3 m/s, more preferably 0.001-0.2 m/s).

The "pre-hydrocarbon pooled" regenerated catalyst leaving the pre-hydrocarbon pooling device 8 enters the dense phase zone 9B (or a transition zone 28 or the conveying pipe 26) at a lower portion of the settling zone 9 of the conversion reactor 1 through a regenerated catalyst conveying pipe 33 (including a control valve 34 and a catalyst distributor (not shown in the figure)) to be mixed with the entrained catalyst, and then passes through a catalyst circulation pipe 31 (including a control valve 32) and enters the reaction zone 22 of the conversion reactor 1 for recycling.

Alternatively, the "pre-hydrocarbon pooled" regenerated catalyst directly enters the reaction zone 22 of the conversion reactor 1 through the regenerated catalyst conveying pipe 33 (including the control valve 34 and the catalyst distributor (not shown in the figure)) for recycling.

Stripping mediums 13, 14, 16, fluidizing mediums 15, 19, and a stripping medium 17 may be steam or other fluids (preferably steam). A stripping medium 18 may be air or other gases (preferably air).

A heat extracting medium 50 may be water, steam or other fluids (preferably water).

In order to better control the reaction temperature of the pre-hydrocarbon pooling device 8, the pre-hydrocarbon pooling device 8 may be provided at an interior or/and an exterior thereof with an internal heat extractor or/and an external heat extractor (not shown in the figure) to maintain the thermal balance of the pre-hydrocarbon pooling reaction system. The reaction temperature of the pre-hydrocarbon pooling device 8 is mainly controlled by adjusting an amount of the regenerated catalyst returned to the pre-hydrocarbon pooling device, or/and a flow rate of a heat extracting medium, or/and a flow rate of a fluidizing medium, or/and other parameters.

In order to realize optimal control of the reaction temperature of the "pre-hydrocarbon pooling" and/or optimal control of the reaction temperature of the downstream conversion reaction of the oxygenate, in the case that the regenerated catalyst stripper 6 is provided upstream of the regenerated catalyst cooler 5, a catalyst mixing buffer space may be provided downstream of the regenerated catalyst cooler 5 to strengthen the mixing of the regenerated catalyst, so that the regenerated catalyst is at a balanced temperature before entering the pre-hydrocarbon pooling device 8, to meet requirements for optimal control of the reaction temperature of the "pre-hydrocarbon pooling" and the reaction temperature of the downstream conversion reactor 1.

The regenerated catalyst stripper 6 (or the catalyst mixing buffer space) may be connected by a pipe.

In order to save space and investment, the regenerated catalyst stripper 6 (or the catalyst mixing buffer space) may also form a one-piece (equal- or variable-diameter) structure with the regenerated catalyst cooler 5 (as shown in FIG. 2). The regenerated catalyst stripper 6 (or the catalyst mixing buffer space) adopts a low-velocity dense-phase fluidized bed having a superficial gas velocity of less than 0.5 m/s (preferably 0.0001-0.3 m/s, more preferably 0.001-0.2 m/s).

Figure 3:
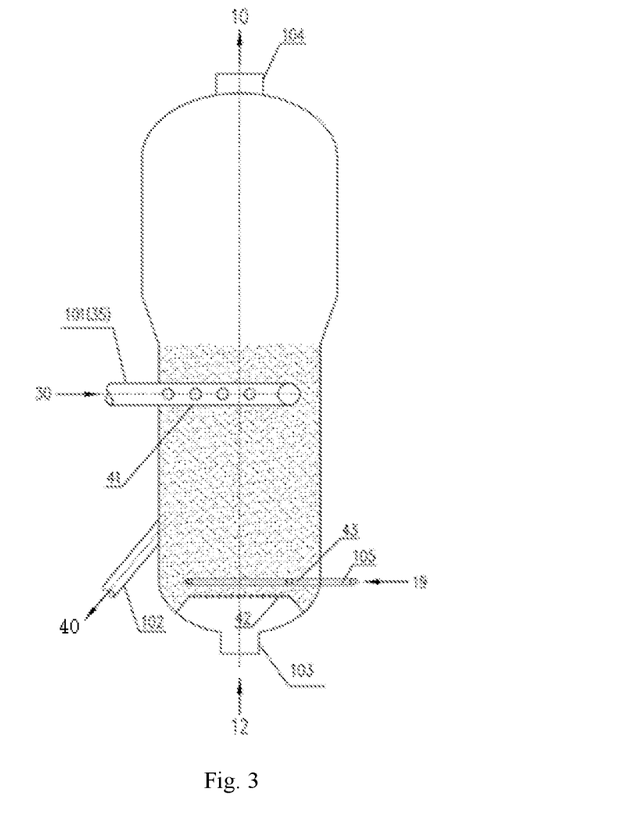

FIG. 3 is a schematic diagram of a catalyst pre-hydrocarbon pooling method and its device according to the present invention (countercurrent contact).

As shown in FIG. 3, the catalyst pre-hydrocarbon pooling (or pre-activation) device of the present invention includes a regenerated catalyst inlet 101 (including a catalyst distributor 41), a regenerated catalyst outlet 102, an activation medium inlet 103 (including a distributor 42), an activation medium outlet 104, or/and a fluidizing medium inlet 105 (including a distributor 43).

A regenerated catalyst 30 from a regenerator enters an upper portion of a pre-hydrocarbon pooling reactor sequentially through a regenerated catalyst conveying pipe 35 (including a control valve and a catalyst distributor, not shown in the figure), the regenerated catalyst inlet 101, and the catalyst distributor 41, and flows downwards to go into countercurrent contact with an activation medium 12 to undergo chemical reactions such as pre-hydrocarbon pooling to form "hydrocarbon pool" active species and a certain amount of carbon deposition, so as to shorten or eliminate an "induction period" of a reaction.

The activation medium 12 enters a bottom of the pre-hydrocarbon pooling reactor sequentially through the activation medium inlet 103 and the distributor 42, and passes through a regenerated catalyst bed from bottom to top. A pre-hydrocarbon pooled reaction gas 10 enters a downstream oxygen-containing mixture conversion reactor (settling zone) through the activation medium outlet 104.

Alternatively, the pre-hydrocarbon pooling reactor may also be provided therein with a first-stage or second-stage cyclone separator. After the pre-hydrocarbon pooled reaction gas is removed of the catalyst entrained therein, the reaction gas enters an inlet of a three-stage cyclone separator.

A "pre-hydrocarbon pooled" regenerated catalyst 40 leaving the pre-hydrocarbon pooling reactor enters a conversion reactor through the "pre-hydrocarbon pooled" regenerated catalyst outlet 102 and a regenerated catalyst conveying pipe 33 (including a control valve and a catalyst distributor, not shown in the figure), for recycling.

In order to better control a reaction temperature of the pre-hydrocarbon pooling reactor, the pre-hydrocarbon pooling reactor may be provided at an interior or/and an exterior thereof with an internal heat extractor or/and an external heat extractor (not shown in the figure) to maintain thermal balance of the pre-hydrocarbon pooling reaction system. The reaction temperature of the pre-hydrocarbon pooling reactor may be controlled by adjusting an amount of the regenerated catalyst returned to the pre-hydrocarbon pooling device, or/and a flow rate of a heat extracting medium, or/and a flow rate of a fluidizing medium, or/and other parameters.

The fluidizing medium 19 may be steam or other fluids (preferably steam). The activation medium 12 is preferably a reaction gas. The heat extracting medium may be water, steam or other fluids (preferably water).

The catalyst distributor may be any industrially used catalyst distributor, and the steam (gas) distributor may be any industrially used gas distributor (including a distribution plate, a distribution pipe, etc.).

Main operating conditions of the pre-hydrocarbon pooling reactor are as follows: a reaction temperature of 300-600° C. (preferably 360-560° C., more preferably 400-530° C.), and contact time of less than 300 minutes (preferably 0.001-200 minutes, more preferably 10-150 minutes).

The pre-hydrocarbon pooling reactor adopts a low-velocity dense-phase fluidized bed having a superficial gas velocity of less than 0.5 m/s (preferably 0.0001-0.3 m/s, more preferably 0.001-0.2 m/s).

Figure 4:
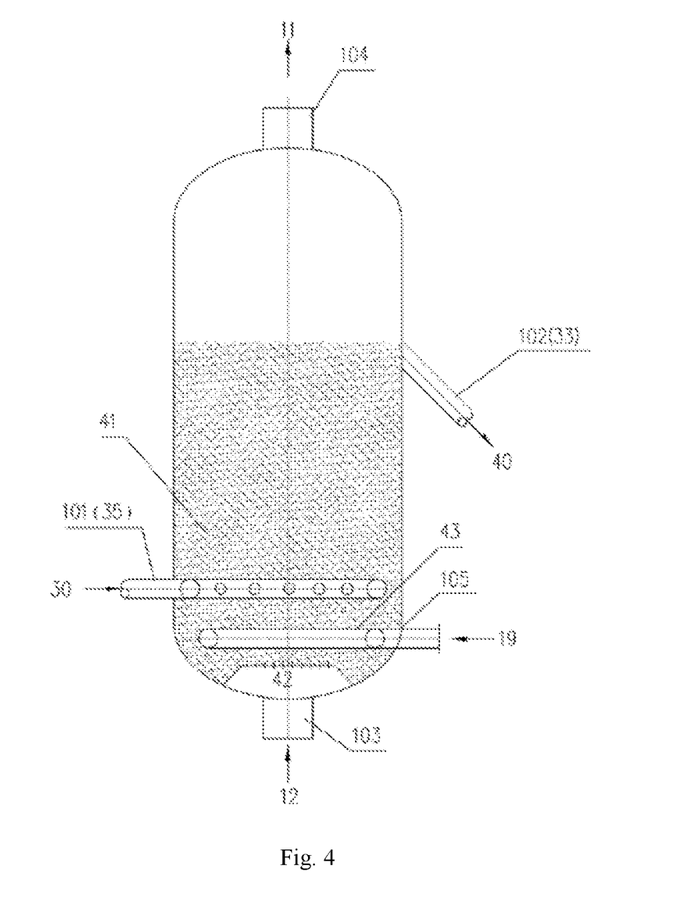

FIG. 4 is a schematic diagram of a catalyst pre-hydrocarbon pooling (or pre-activation) method and its device according to the present invention (co-current contact).

As shown in FIG. 4, the catalyst pre-hydrocarbon pooling (or pre-activation) device of the present invention includes a regenerated catalyst inlet 101 (including a catalyst distributor 41), a regenerated catalyst outlet 102, an activation medium inlet 103 (including a distributor 42), an activation medium outlet 104, or/and a fluidizing medium inlet 105 (including a distributor 43).

A regenerated catalyst 30 from a regenerator enters a bottom of the pre-hydrocarbon pooling reactor sequentially through a regenerated catalyst conveying pipe 35 (including a control valve and a catalyst distributor, not shown in the figure), the regenerated catalyst inlet 101, and the catalyst distributor 41. An activation medium 12 enters the bottom of the pre-hydrocarbon pooling reactor sequentially through the activation medium inlet 103 and the distributor 42. The regenerated catalyst 30 and the activation medium 12 flow co-current, from bottom to top, through a regenerated catalyst bed to undergo chemical reactions such as pre-hydrocarbon pooling to form "hydrocarbon pool" active species and a certain amount of carbon deposition, so as to shorten or eliminate an "induction period" of a reaction.

A pre-hydrocarbon pooled reaction gas enters a downstream oxygen-containing mixture conversion reactor (settling zone) through the activation medium outlet 104.

A "pre-hydrocarbon pooled" regenerated catalyst 40 leaving the pre-hydrocarbon pooling reactor enters a conversion reactor through the "pre-hydrocarbon pooled" regenerated catalyst outlet 102 and a regenerated catalyst conveying pipe 33 (including a control valve and a catalyst distributor, not shown in the figure), for recycling.

In order to better control a reaction temperature of the pre-hydrocarbon pooling reactor, the pre-hydrocarbon pooling reactor may be provided at an interior or/and an exterior thereof with an internal heat extractor or/and an external heat extractor (not shown in the figure) to maintain thermal balance of the pre-hydrocarbon pooling reaction system. The reaction temperature of the pre-hydrocarbon pooling reactor may be controlled by adjusting an amount of the regenerated catalyst returned to the pre-hydrocarbon pooling device, or/and a flow rate of a heat extracting medium, or/and a flow rate of a fluidizing medium, or/and other parameters.

The fluidizing medium 19 may be steam or other fluids (preferably steam). The activation medium 12 is preferably a reaction gas. The heat extracting medium may be water, steam, or other fluids (preferably water).

The catalyst distributor may be any industrially used catalyst distributor, and the steam (gas) distributor may be any industrially used gas distributor (including a distribution plate, a distribution pipe, etc.).

Main operating conditions of the pre-hydrocarbon pooling reactor are as follows: a reaction temperature of 300-600° C. (preferably 360-560° C., more preferably 400-530° C.), and contact time of less than 300 minutes (preferably 0.001-200 minutes, more preferably 10-150 minutes).

The pre-hydrocarbon pooling reactor adopts a low-velocity dense-phase fluidized bed having a superficial gas velocity of less than 0.5 m/s (preferably 0.0001-0.3 m/s, more preferably 0.001-0.2 m/s).

Example 1

In Example 1, methanol is used as the oxygenate raw material, and a process flow shown in FIG. 2 is adopted. SAPO-34 is used as the catalyst. The methanol conversion reactor and the regenerator are both operated under conventional conditions. A reaction gas is used as the activation medium. Main operating conditions of the pre-hydrocarbon pooling device are as follows: a superficial linear velocity of 0.1-0.2 m/s, a reaction temperature of 460° C., and contact time of 60-80 minutes.

Here, hydrocarbon pool active species on the regenerated catalyst after pre-hydrocarbon pooling are substantially recovered and a reasonable level of carbon deposition is formed. Simulation calculation results show that compared with the existing MTO technology, the present invention, with the addition of the pre-hydrocarbon pooling device of the present invention, improves the selectivity to low-carbon olefins ($C_2^= + C_3^=$) by 5.7 percentage points.

A comparison of main parameters and effects is shown in Table 1.

TABLE 1

| Parameters | Existing MTO technology | Present invention |
|---|---|---|
| Temperature of conversion reaction ° C. | 480 | 480 |
| Temperature of regeneration ° C. | 680 | 680 |
| Catalyst/methanol ratio weight/weight | 0.23 | 0.23 |
| Coke on regenerated catalyst % | 2.3 | 2.3 |
| Regenerated catalyst cooler | No | Yes |
| Temperature of cooled regenerated catalyst ° C. | | 460 |
| Pre-hydrocarbon pooling device | No | Yes |
| Temperature of pre-hydrocarbon pooling reaction ° C. | | 460 |
| Selectivity to low-carbon olefins ($C_2^=+C_3^=$) % | 79.8 | 85.5 |

Example 2

In Example 2, methanol is used as the oxygenate raw material, and a process flow shown in FIG. 2 is adopted. SAPO-34 is used as the catalyst. The methanol conversion reactor and the regenerator are both operated under conventional conditions. A reaction gas is used as the activation medium. Main operating conditions of the pre-hydrocarbon pooling device are as follows: a superficial linear velocity of 0.1-0.2 m/s, a reaction temperature of 460° C., and contact time of 30-40 minutes.

Simulation calculation results show that compared with the existing MTO technology, the present invention, with the addition of the pre-hydrocarbon pooling device of the present invention, improves the selectivity to low-carbon olefins ($C_2^=+C_3^=$) by 3.1 percentage points.

A comparison of main parameters and effects is shown in Table 2.

TABLE 2

| Parameters | Existing MTO technology | Present invention |
|---|---|---|
| Temperature of conversion reaction ° C. | 480 | 480 |
| Temperature of regeneration ° C. | 680 | 680 |
| Catalyst/methanol ratio weight/weight | 0.23 | 0.23 |
| Coke on regenerated catalyst % | 2.3 | 2.3 |
| Regenerated catalyst cooler | No | Yes |
| Temperature of cooled regenerated catalyst ° C. | | 460 |
| Pre-hydrocarbon pooling device | No | Yes |
| Temperature of pre-hydrocarbon pooling reaction ° C. | | 460 |
| Selectivity to low-carbon olefins ($C_2^= + C_3^=$) % | 79.8 | 82.9 |

The invention claimed is:

1. A method for improving selectivity of conversion of an oxygenate to low-carbon olefins, wherein a regenerated catalyst from a regenerator enters a pre-hydrocarbon pooling device where the regenerated catalyst mixes with an activating medium to undergo a pre-hydrocarbon-pooling reaction, forming a "hydrocarbon pool" active species capable of selective catalyzing of a conversion reaction of an oxygenate to low-carbon olefin, and a pre-hydrocarbon-pooled regenerated catalyst leaving the pre-hydrocarbon-pooling device enters a conversion reactor for cycling.

2. The method according to claim 1, wherein main operating conditions of the pre-hydrocarbon-pooling device are: a reaction temperature of 300-600° C. and contact time of less than 300 minutes.

3. The method according to claim 1, wherein main operating conditions of the pre-hydrocarbon-pooling device are: a reaction temperature of 360-560° C. and contact time of 0.001-200 minutes.

4. The method according to claim 1, wherein main operating conditions of the pre-hydrocarbon-pooling device are: a reaction temperature of 400-530° C. and contact time of 10-150 minutes.

5. The method according to claim 1, wherein the pre-hydrocarbon-pooling device adopts a low-velocity dense-phase fluidized bed reactor having a superficial gas velocity of less than 0.5 m/s.

6. The method according to claim 1, wherein the pre-hydrocarbon-pooling device adopts a low-velocity dense-phase fluidized bed reactor having a superficial gas velocity of 0.0001-0.3 m/s.

7. The method according to claim 1, wherein the pre-hydrocarbon-pooling device adopts a low-velocity dense-phase fluidized bed reactor having a superficial gas velocity of 0.001-0.2 m/s.

8. The method according to claim 1, wherein the activating medium is any one, two or more of an oxygenate raw material, a reaction product, a hydrocarbon, and other oxygenates, or a mixture thereof, wherein: the oxygenate raw material is any one, two or more of methanol, ethanol, dimethyl ether, and methyl ethyl ether, or a mixture thereof; the reaction product is a reaction gas that has not undergone a separation or has been removed of part or all entrained catalyst by a first-stage separator or multiple stages of separators, or a reaction gas that has undergone a heat exchange, quenching, or water washing, or a reaction gas from a downstream olefin product separation unit pressurized by a reaction gas compressor, or a stripping gas from a top of a sewage stripper, or any one, two or more of the foregoing, or a mixture thereof; the hydrocarbon is any one, two or more of products from the downstream olefin product separation unit, including ethylene, propylene, ethane, propane, mixed C4, C5+ fractions, and fuel gases, or a mixture thereof, or is any one, two or more of olefins, aromatic hydrocarbons, alkanes, or a mixture thereof; and the other oxygenates are any one, two or more of any organic oxygenates, or a mixture thereof.

9. The method according to claim 1, wherein the pre-hydrocarbon pooling device is disposed with an internal heat extractor or/and an external heat extractor.

10. The method according to claim 1, wherein a regenerated catalyst cooler is disposed before the regenerated catalyst enters the pre-hydrocarbon-pooling device, so as to cool the regenerated catalyst to 200-630° C., and a reaction temperature of the pre-hydrocarbon-pooling device is controlled mainly by adjusting an amount of the regenerated catalyst returned to the pre-hydrocarbon pooling device or/and a flow rate of a heat extracting medium or/and a flow rate of fluidizing medium.

11. The method according to claim 1, wherein a regenerated catalyst cooler is disposed before the regenerated catalyst enters the pre-hydrocarbon-pooling device, so as to cool the regenerated catalyst to 300-600° C.

12. The method according to claim 1, wherein a regenerated catalyst cooler is provided upstream of a regenerated catalyst stripper, the regenerated catalyst cooler and the regenerated catalyst stripper together form an equal-diameter or variable-diameter one-piece structure.

13. The method according to claim 12, wherein the regenerated catalyst cooler and/or the regenerated catalyst stripper each adopt a low-velocity dense-phase fluidized bed having a superficial gas velocity of less than 0.5 m/s.

14. The method according to claim 12, wherein the regenerated catalyst cooler and/or the regenerated catalyst stripper each adopt a low-velocity dense-phase fluidized bed having a superficial gas velocity of 0.0001-0.3 m/s.

15. The method according to claim 12, wherein the regenerated catalyst cooler and/or the regenerated catalyst stripper each adopt a low-velocity dense-phase fluidized bed having a superficial gas velocity of 0.001-0.2 m/s.

16. A device for improving selectivity of conversion of an oxygenate to low-carbon olefins, comprising a pre-hydrocarbon-pooling device.

17. The device according to claim 16, further comprising a regenerated catalyst cooler and/or a regenerated catalyst stripper.

18. The device according to claim 16, wherein the pre-hydrocarbon-pooling device adopts any one, two or more of industrially used reactors including fluidized bed reactors, or a combination thereof, wherein the fluidized bed reactors include bubbling bed reactors, turbulent bed reactors, fast bed reactors, or riser reactors, and the like, wherein the riser reactors may be any industrially used equal-diameter or variable-diameter riser reactors.

19. The method according to claim 9, wherein the pre-hydrocarbon-pooling device adopts a low-velocity dense-phase fluidized bed reactor having a superficial gas velocity of less than 0.5 m/s.

20. The method according to claim 10, wherein the pre-hydrocarbon-pooling device adopts a low-velocity dense-phase fluidized bed reactor having a superficial gas velocity of less than 0.5 m/s.

* * * * *